United States Patent [19]

Ahmed

[11] Patent Number: 5,795,902
[45] Date of Patent: Aug. 18, 1998

[54] 3-SUBSTITUTED 2-OXINDOLE-1 CARBOXAMIDE PHARMACEUTICAL COMPOSITIONS

[75] Inventor: Imram Ahmed, Gales Ferry, Conn.

[73] Assignee: Pfizer Inc., New York, N.Y.

[21] Appl. No.: 715,748

[22] PCT Filed: Sep. 2, 1993

[86] PCT No.: PCT/US93/08063

§ 371 Date: Apr. 6, 1995

§ 102(e) Date: Apr. 6, 1995

[87] PCT Pub. No.: WO94/07488

PCT Pub. Date: Apr. 14, 1994

Related U.S. Application Data

[63] Continuation of Ser. No. 416,721, filed as PCT/US93/08063 Apr. 6, 1995, published as WO94/07488 Apr. 14, 1994, abandoned.

[51] Int. Cl.⁶ .................................................. A61K 31/40
[52] U.S. Cl. ........................... 514/354; 514/434; 514/418; 514/912; 514/814; 514/415; 514/419; 514/414
[58] Field of Search ........................... 514/354, 434, 514/418, 912, 814, 415, 419, 414

[56] References Cited

U.S. PATENT DOCUMENTS 4,918,103  4/1990  Park et al. ........................ 514/340

FOREIGN PATENT DOCUMENTS 0448253  7/1991  European Pat. Off. .

*Primary Examiner*—Keith D. MacMillan
*Attorney, Agent, or Firm*—Peter C. Richardson; Paul H. Ginsburg; Garth Butterfield

[57] ABSTRACT

The present invention relates to a pharmaceutical preparation comprising: (A) at least one triglyceride or propylene glycol diester of fractionated coconut oil fatty acids; and (B) at least one carboxamide compound of the formula I. The composition renders the carboxamides of formula I more storage-stable and less susceptible to hydrolysis. Methods of using the composition to inhibit activation of collagenase, treating inflammatory disease, and eliciting an analgesic response are also disclosed.

3 Claims, No Drawings

3-SUBSTITUTED 2-OXINDOLE-1-CARBOXAMIDE PHARMACEUTICAL COMPOSITIONS

This is a continuation, of application Ser. No. 08/416,721, filed on Apr. 6, 1995, abandoned.

BACKGROUND OF THE INVENTION

This invention relates to pharmaceutical compositions comprising certain 3-substituted 2-oxindole-1-carboxamides and medium chain ($C_8$ to $C_{10}$) fatty acid triglyceride and propylene glycol diesters. These carboxamides are useful as analgesics for use in mammals such as man and in ameliorating or alleviating pain encountered while recovering from surgery or other trauma or in eliminating the symptoms of chronic diseases such as inflammation and pain associated with rheumatoid arthritis and osteoarthritis, as shown in U.S. Pat. Nos. 4,556,672 and 5,047,554. The carboxamides are also useful for treating collagenase mediated disorders and diseases, such as bone resorption disorders, corneal ulceration, periodontal disease, inflammatory diseases, and wounds of the skin and burns in a mammal, as shown in U.S. Pat. No. 5,008,283.

The carboxamides described in formula I are chemically unstable in water. It is known that the rate of hydrolytic degradation may be reduced by protection of labile drugs e.g. sequestration in the hydrophobic core of micelles or formulation in low water activity, non-aqueous solvent-based vehicles i.e. essential oils. In addition to hydrolytic instability the carboxamides are also prone to oxidative degradation in aqueous e.g. water, and non-aqueous e.g. oils, vehicles. Oxidative instability can be reduced in saturated oils by inclusion of antioxidants or by formulation in unsaturated oils which protect the drug by being preferentially oxidized themselves. However, the carboxamides described in formula I are not readily stabilized in oils commonly used in pharmaceutical preparations e.g. sesame oil, peanut oil, safflower oil, cottonseed oil.

SUMMARY OF THE INVENTION

The present invention relates to a pharmaceutical preparation comprising:

(A) at least one triglyceride or propylene glycol diester of fractionated coconut oil fatty acids; and (B) at least one compound of the formula

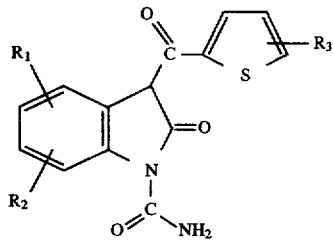

I where $R_1$, $R_2$, and $R_3$ are each independently hydrogen, fluoro, bromo, or chloro, or a pharmaceutically acceptable salt thereof, wherein the weight ratio of (A) to (B) ranges from 5.6 to 999.

The pharmaceutical preparation includes 85 to 99% by weight of (A) and 0.1 to 15% by weight of (B).

Preferably, $R_1$, $R_2$, and $R_3$ are each independently fluoro or chloro.

Preferred compounds of formula I include:

5-chloro-2,3-dihydro-2-oxo-3-(2-thienylcarbonyl)-indole-carboxamide;

6-chloro-5-fluoro-2,3-dihydro-2-oxo-3-(2-thienylcarbonyl)-in-dole-carboxamide; and 6-chloro-5-fluoro-2,3-dihydro-2-oxo-3-(2-(4-chloro)-thienyl-carbonyl)-indole-carboxamide.

The present invention also includes a method of inhibiting activation of collagenase.

The present invention also includes a method of treating an inflammatory disease.

The present invention also includes a method of eliciting an analgesic response.

DETAILED DESCRIPTION OF THE INVENTION

It has been found that pharmaceutical preparations including the carboxamides of formula I and $C_8$ to $C_{10}$ saturated fatty acid triglycerides and propylene glycol diesters have superior product viability and shelf life. As the result of utilizing such a formulation, the carboxamides are less susceptible to hydrolysis and oxidation which can deteriorate them and ultimately render them ineffective. Stabilization of the carboxamides in these preparations do not require the addition of an antioxidant or other auxiliary stabilizers.

The triglycerides used in the claimed invention are neutral oils which are composed of esters of medium chain ($C_8$ to $C_{10}$) fatty acids, also referred to as fractionated coconut oil. These fatty acids are esterified with either glycerin or propylene glycol and are sold under the name MIGLYOL® (i.e. MIGLYOL® 810, MIGLYOL® 812, and MIGLYOL® 840). MIGLYOLS are also described as triglycerides of fractionated coconut oil fatty acids or caprylic acid/capric acid triglycerides. Fractionated coconut oil is prepared from the fixed oils obtained from the dried solid part of the endosperm of Cocos nucifera L by hydrolysis, fractionation of the liberated fatty acids and re-esterification with glycerol or propylene glycol. It consists of a mixture of short and medium-chain saturated fatty acids, mainly octanoic and decanoic acids. Miglyol® is the trade name for fractionated coconut oil or caprylic acid/capric acid triglycerides from Dynamit Nobel Ltd., Germany and the U.K. These vehicles have demonstrated stability against oxidation and rancidification as well as outstanding safety and biocompatibility. Furthermore, since only saturated fatty acids are used the oils do not generate peroxides or other free radicals which could destabilize the pharmaceutical contained therein. The low water content also minimizes the hydrolysis of the carboxamide. In the preferred composition, a carboxamide of formula I is dispersed in an oil vehicle comprising Miglyol® 812 and other oil-soluble additives described below under agitation to produce a homogenous suspension of the drug substance in the oil vehicle.

Other additives which can be present in the pharmaceutical preparation can include an anticaking agent such as, for example, propylene glycol, polyethylene glycol, glycerin, sorbitol, benzyl alcohol, lecithin, or aluminum stearate. The amount of anticaking agent can range from approximately 0.05 to 5% by weight. The pharmaceutical preparation can also contain preservative in an amount ranging from 0.5 to 2.0% by weight. Such preservatives can include, for example, phenol, benzyl alcohol, parabens, chlorbutanol, and benzyl benzoate. Gelling agents, such as aluminum monostearate can also be included in the pharmaceutical preparation in an amount ranging from 0.5 to 3.0% by volume.

The stability of these pharmaceutical preparations can be evaluated, for example, under accelerated storage conditions after subjecting suspensions of the carboxamides (6% by weight of the drug substance) packaged in glass vials to high temperatures of up to 70° C. for up to nine weeks. During the stability challenge the level of intact drug remaining in the preparation, as well as hydrolytic and oxidative decomposition products is quantified by high performance liquid chromatography (HPLC). For assay, the suspension is diluted with methanol/triethylamine 100/1 volume-by-volume to give a final drug concentration of 0.6 to 1.2 mg/mL. This solvent dissolves the suspended drug to produce a solution which can be directly injected on the HPLC column. For chromatography, the mobile phase is methanol/water 90/10 v/v +1% triethylamine, the column is a reversed phase octadecasilane and the solvent flow rate was 1 mL/minute. Drug detection was by UV absorbance at 246 nm. Such an assay has shown there to be virtually no decomposition of carboxamide in suspension after nine weeks.

When a compound of formula I or salt thereof is used in a human subject, the daily dosage will normally be determined by the prescribing physicians. Moreover, the dosage will vary according to the age, weight and response of the individual patient, as well as the severity of the patient's symptoms and the potency of the particular compound being administered. However, for acute administration to relieve pain, an effective dose in most instances will be 0.01 to 0.25 g as needed (e.g., one- to four-times-a-day). For chronic administration, in most instances an effective dose will be from 0.01 to 0.5 g per day, and preferably 0.1 to 0.25 g per day in single or divided doses. On the other hand, it may be necessary to use dosages outside these limits in some cases.

Preferably the pharmaceutical compositions of the present invention are parenteral pharmaceutical compositions. The pharmaceutical compositions of this invention may be produced by formulating a compound of formula I (as the active ingredient) in dosage unit form. Some examples of dosage unit forms are sterile suspensions for intramuscular, subcutaneous or intra-articular injection, sterile ophthalmic suspensions for topical application to the eye, capsules for oral administration, rectal suppositories, or topical lotion for application to the skin or scalp.

An example of a suitable pharmaceutical dosage for oral administration are soft gelatin capsules. Orally administered suspensions can be delivered, e.g., upon encapsulation of a suspension of compound I in the oil, i.e. Miglyol 812, in a soft gelatin capsule. A rectal suppository may be formulated by dispersing the carboxamide in a neutral oil along with compatible suppository bases, such as cocoa butter or Whitepsol W35, which have melting points above body temperature. A topical product for application to the skin would contain the carboxamide as the active agent dispersed in the neutral oil, e.g., Miglyol 812, and also containing one or more pharmaceutical inactive ingredients, such as: cetyl alcohol, stearic acid, propylene glycol, aluminum monostearate, benzyl alcohol, as diluents and preservatives. A parenteral composition is preferably a suspension of the carboxamide in the neutral oil, and may also contain other inactive pharmaceutical components, such as: benzyl alcohol as preservative, aluminum monostearate as a gelling agent and propylene glycol as a dispersing agent.

The following Example illustrates how the pharmaceutical preparations can be prepared. Commercial reagents can be utilized without further purification.

EXAMPLE 1

800 mL of Miglyol 812 was heated to 45° C. in a compounding vessel equipped with an agitator and homogenizer. 10 g of benzyl alcohol was added to the oil under agitation (about 60–80 R.P.M.). The oil solution was sterile filtered into a sterile compounding vessel equipped wait an agitator and homogenizer. 120 g of micronized, sterile carboxamide powder was dispersed into the oil phase under agitation. The suspension was homogenized under high shear for ten minutes and then was allowed to cool to room temperature under mild agitation (60–80 R.P.M.). The suspension was brought to a total batch weight of 1000 grams with the addition of the required amount of sterile Miglyol 812 to the suspension to give a final concentration of 12% by weight of carboxamide in the final formulation. The suspension was aseptically filled into 50 cc, Type I, flint glass vials using an automated filling apparatus. The vials were capped with teflon-coated rubber stoppers and crimped with aluminum shells.

EXAMPLE 2

800 mL of Miglyol 812 was heated to 45° C. in a compounding vessel equipped with an agitator and homogenizer. 10 g of benzyl alcohol was added to the oil under agitation (˜60–80 R.P.M.). The oil solution was sterile filtered into a sterile compounding vessel equipped with an agitator and homogenizer. 20 g of sterile, aluminum monostearate powder was added to the oil solution in divided portions under agitation to gel the oil. The gelled oil was allowed to cool to room temperature and allowed to stand for six hours without agitation. 120 g micronized, sterile carboxamide powder was then dispersed into the gelled oil under agitation. The suspension was brought to a total batch weight of 1000 grams with the addition of the required amount of sterile, gelled Miglyol 812 to the suspension to give a final concentration of 12% by weight of carboxamide in the final formulation. The suspension was aseptically filled into 50 cc, Type I, flint glass vials using an automated filling apparatus. The vials were capped with teflon-coated rubber stoppers and crimped with aluminum shells.

EXAMPLE 3

800 mL of Miglyol 812 was heated to 45° C. in a compounding vessel equipped with an agitator and homogenizer. 10 g of benzyl alcohol was added to the oil under agitation (about 60–80 R.P.M.). 120 g of micronized, sterile carboxamide powder was dispersed into the oil phase under agitation. The suspension was homogenized under high shear for ten minutes and then was allowed to cool to room temperature under mild agitation (60–80 R.P.M.). The suspension was brought to a total batch weight of 1000 grams with the addition of the required amount of Miglyol 812 to the suspension to give final concentration of 12% by weight carboxamide in the final formulation. The suspension was filled into soft gelatin capsules using an automated filling apparatus for oral ingestion.

EXAMPLE 4

200 g of Miglyol 812 and 800 g of Whitepsol W35 were heated to 60° C. in a compounding vessel equipped with an agitator and homogenizer. Carboxamide powder was dispersed into the resulting oil solution under agitation. The suspension was allowed to filled into suppository molds and congealed by cooling to room temperature.

I claim:

1. A pharmaceutical preparation comprising:
   (A) at least one triglyceride or propylene glycol diester of fractionated coconut oil fatty acids, wherein said coconut oil fatty acids include $C_8$ to $C_{10}$ fatty acids; and (B) at least one compound of the formula

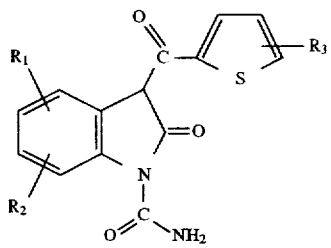

where $R_1$, $R_2$, and $R_3$ are each independently hydrogen, fluoro, bromo, or chloro, or a pharmaceutically acceptable salt thereof, wherein the ratio of % by weight of (A) to % by weight of (B) ranges from 5.6 to 999.

2. The pharmaceutical preparation of claim 1, wherein the compound of formula I is 5-chloro-2,3-dihydro-2-oxo-3-(2-thienyl-carbonyl)-indole-carboxamide.

3. The pharmaceutical preparation of claim 1, wherein said coconut oil fatty acids comprises caprylic acid, caproic acid, lauric acid, and linoleic acid.

* * * * *